United States Patent [19]

Henley-Cohn et al.

[11] 4,439,872

[45] Apr. 3, 1984

[54] APPARATUS TO ASSIST ESOPHAGEAL SPEECH

[76] Inventors: Julian L. Henley-Cohn, 60 Lincoln St., New Haven, Conn. 06005; Eugene R. Jakubczak, 606 S.E. Boutell Bay City, Mich. 48706

[21] Appl. No.: 309,097

[22] Filed: Oct. 6, 1981

[51] Int. Cl.³ .............................................. A61F 1/20
[52] U.S. Cl. ................................................. 3/1.3; 3/1
[58] Field of Search ....................... 3/1, 1.3, 1.4, 1.5; 128/214.4, 80 C, 283, 207.14; 137/847; 46/178

[56] References Cited

U.S. PATENT DOCUMENTS

| | | | |
|---|---|---|---|
| 1,266,856 | 5/1918 | Ramsay | 128/207.14 |
| 2,274,897 | 3/1942 | Horne | 46/178 |
| 2,576,192 | 11/1951 | Poznik | 137/847 |
| 3,074,400 | 1/1963 | Schulman | 128/80 C |
| 3,221,742 | 12/1965 | Orowan | 128/283 |
| 3,334,631 | 8/1967 | Stebleton . | |
| 3,405,843 | 10/1968 | Waston, Jr. | 137/846 |
| 3,499,450 | 3/1970 | Rathjen . | |
| 3,766,915 | 10/1973 | Rychlik | 128/214.4 |
| 3,924,637 | 12/1975 | Swanson . | |
| 4,044,402 | 8/1977 | Edwards . | |
| 4,060,856 | 12/1977 | Edwards . | |
| 4,189,546 | 2/1980 | Deichert et al. | 3/1.4 |
| 4,223,411 | 9/1980 | Schoendorfer et al. . | |
| 4,253,201 | 3/1981 | Ross et al. | 3/1 |
| 4,363,320 | 12/1982 | Kossoue | 128/207.14 |

OTHER PUBLICATIONS

"Extirpation of the Larynx", *Scientific American*, Supplement #115, pp. 1834-1835, Mar. 16, 1878.
"Improved Silastic Tracheostomy Tubes for Infants & Young Children", *Journal of Pediatric Surgery*, vol. 3, No. 3, 6/68.
"New Surgery Technique Helps Man Speak Again", *New Haven Register*, front page, 10/6/80.
"A New Flexible Silicone Rubber Tracheostomy Tube", *The American Journal of Surgery*, vol. 114, No. 4, pp. 551-552, 10/67.
"Silastic Tracheostomy Tube (Aberdeen Design)" Dow Corning Bulletin 14-414A, Feb. 1970.
"Silastic Tracheostomy Tube (Moore Design)", Dow Corning Bulletin 51-246, Feb. 1975.
"Blom-Singer Voice Prosthesis Bulletin", *Bivona Surgical Device*.
"Surgical-Prosthetic Approaches for Postlaryngectomy Voice Restoration" by Blom & Singer, presented Apr. 29-May 3, 1979.
"Speech After Laryngectomy the Voice Button Fistula Procedure" Brochure by William R. Panje, M.D.

*Primary Examiner*—Richard J. Apley
*Assistant Examiner*—Dave Isabella
*Attorney, Agent, or Firm*—Pennie & Edmonds

[57] ABSTRACT

An apparatus to assist esophageal speech in an individual who has undergone a laryngectomy who has a tracheastome and a tracheal-esophageal fistula. The apparatus comprising an elastomeric tube with an open tracheal end and an esophageal end having a one-way slit valve normally closed which allows air to be diverted from the trachea to the esophagus when the tracheastome is sealed and the patient exhales. The elastomeric air tube has an elliptical cross section which contributes to higher rates of air flow and comfortable expiration pressures by reducing the bending movement of the portions of the tube located on either side of the slit or flapper valve. The contacting surfaces of the slit valve are coated with an adhesion-reducing compound to further reduce opening pressure. A retaining flange formed in a plane extending generally perpendicularly from the air tube does not cover the portion of the neck having the tracheastome, thus forming no significant obstruction to breathing. A malleable planer material is embedded in the flange. The flange is formed in a generally V-shape to avoid the cleidomastoid neck muscles thus reducing the tendency of the device to be ejected.

6 Claims, 10 Drawing Figures

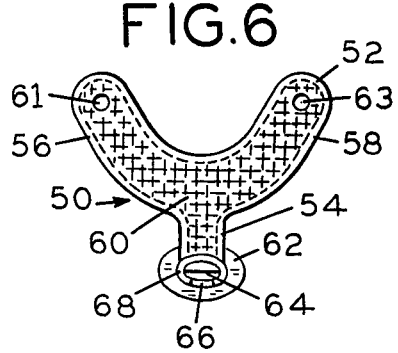
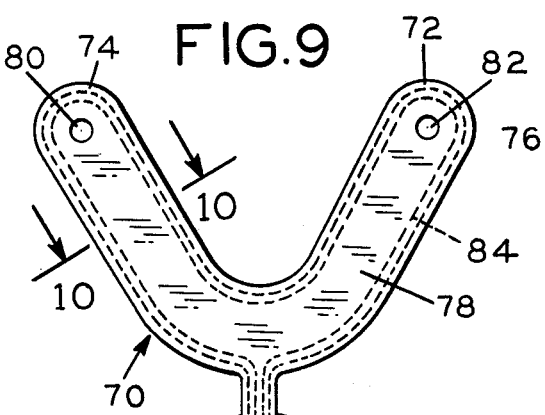
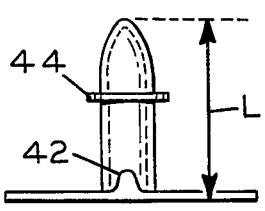
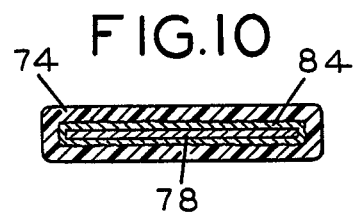
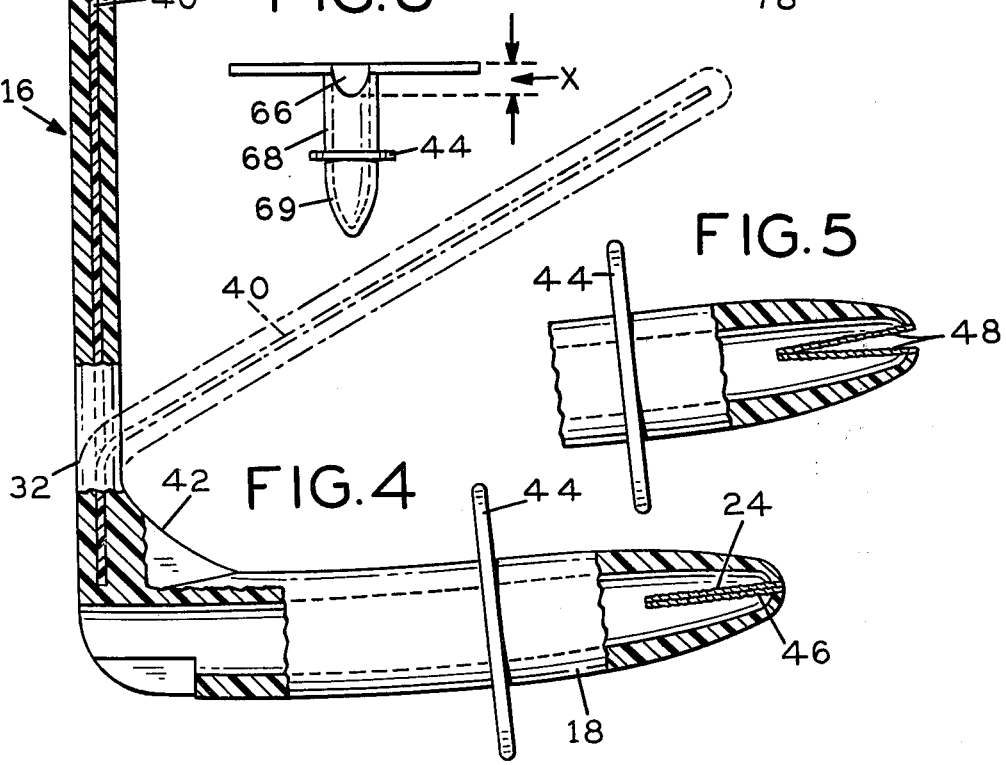

APPARATUS TO ASSIST ESOPHAGEAL SPEECH

TECHNICAL FIELD

This invention relates to devices which are used to assist esophageal speech in those individuals who have undergone a laryngectomy. More particularly, it relates to devices which pass air from the trachea to the esophagus causing the walls of the esophagus to vibrate as air is exhaled through the mouth and aiding in the production of speech.

BACKGROUND ART

A variety of surgical techniques and devices have been proposed to assist an individual who has undergone a laryngectomy in producing relatively normal-sounding speech. For example, electronic devices which produce a generally monotonal output modulated by the vibrations received from a transducer held to the throat have been developed. This speech is rather mechanical sounding and does not approach the normal quality of human speech.

The more effective techniques for producing natural-sounding speech use the esophagus as a substitute for the larynx which has been removed. The walls of the esophagus are caused to vibrate by air which is introduced into the esophagus and then passes through the remainder of the speech tract and out through the mouth.

It is possible for some individuals to master an esophageal speech technique in which quantities of air are periodically swallowed and then released to vibrate the esophagus. This technique is difficult to master and produces speech which of necessity is limited to one or two words for each quantity of air swallowed.

Various laryngeal protheses have been proposed since the latter part of the nineteenth century. Dr. David Foulis in *Scientific American*, Supplement No. 115, Mar. 16, 1878, pp. 1834 to 1835 reported on a device used to bypass air from the trachea to the esophagus containing a reed which vibrated due to air flow. The speech produced by the use of such a device, however, had the monotonal qualities of the vibrating reed.

U.S. Pat. Nos. 4,060,402 and 4,060,856 to Nigel disclose a laryngeal prothesis of a generally symmetrical form comprising a hollowed main body with external tubes to fit into the trachea and a surgically-formed fistula intended to serve as a pseudo-glottis. A short fistular tube is configured with a free end formed of a thin-walled, normally collapsed tubular one-way valve (See column 3, lines 7-15) which is designed to prevent undesired reflux of saliva into the trachea but opens in response to air pressure produced by expiration, thus passing diverted air to the pharynx for phonation. This device is rather complex and the surgically-created openings and cavities required to use the device are subject to breakdown with the passage of time. In addition, the surgical techniques necessary may be contraindicated for many patients.

A much simpler device, the voice-button prosthesis developed by Dr. William R. Panje may be inserted in a surgically created tracheal-esophageal fistula. This device comprises a short tube having two closely-spaced flanges which serve to hold the device in place so that one end of the tube and one flange associated with this end are disposed within the esophagus and the other end of the tube and one flange which is associated with that end are disposed within the trachea. The esophageal end contains a one-way slit valve which permits air to travel from the trachea to the esophagus when the tracheal opening or stoma is sealed and the patient exhales.

Despite the presence of the flanges this type of device is ocassionally subject to ejection during violent movement of the anatomical structures due to, for example, coughing. In addition a substantial amount of air pressure is generally required to produce a sufficiently high volume of air flow to produce high quality speech.

DISCLOSURE OF THE INVENTION

The present invention solves the above-mentioned problems by providing an apparatus suitable for use in the rather harsh wet and mechanically mobile environment of the trachea. It comprises an elastomeric air tube with an open tracheal end and a normally-closed esophageal end having a one-way slit valve. Air flow through this one-way slit valve is significantly higher than that in prior art devices at comfortable expiration pressures above those necessary to open the valve. Configuring the air tube with an elliptical cross-section and forming the slit valve by cutting in the longitudinal direction along the tube contribute to a reduced bending moment which facilitates opening of the valve.

To prevent adhesion of the surfaces of the slit valve, the contacting surfaces are coated with an adhesion reducing compound. Further, the surfaces are buffed or roughened so as to reduce the total contacting surface area, thus further reducing adhesion.

A flange which is formed in a plane extending generally perpendicularly from the air tube is adapted to occupy a small portion of that plane and have a surface which lies on an external portion of the neck without covering the portion of the neck having the tracheostome. As a result, there is no significant blockage of the opening used for breathing.

The apparatus of the invention is formed with a malleable planar material embedded in the flange parallel to the surface which is adapted to lie on the neck. This material may be a metal mesh, a thin metal sheet, or a thermoformed plastic. The flange fits snuggly against the neck and being larger than the stoma it prevents aspiration and reduces the possibility of ejection by being configured so as to avoid the area of the neck associated with certain neck muscles.

BRIEF DESCRIPTION OF THE DRAWINGS

FIG. 4 is an enlarged side elevational view of the apparatus of the invention in partial cross section with the slit valve closed.

FIG. 5 shows the esophageal end of the apparatus as shown in FIG. 4 with the slit valve open.

FIG. 6 is an end view of an additional embodiment of the apparatus.

FIG. 7 is a plan view of the apparatus shown in FIG. 6.

FIG. 8 is an underside plan view of the apparatus shown in FIG. 6.

FIG. 9 is an enlarged view of yet another embodiment of the invention.

FIG. 10 is a cross sectional view taken along line 10—10 of FIG. 9.

DETAILED DESCRIPTION OF THE INVENTION

Surgical removal of the larynx is often necessitated by the existence of some pathological condition such as a malignancy. When this procedure is utilized, the trachea may not be left with an upwardly-pointing opening within the neck because material swallowed during the process of eating or saliva would tend to fall into the trachea and then the lungs, causing severe coughing or asphixiation.

Figure 1:
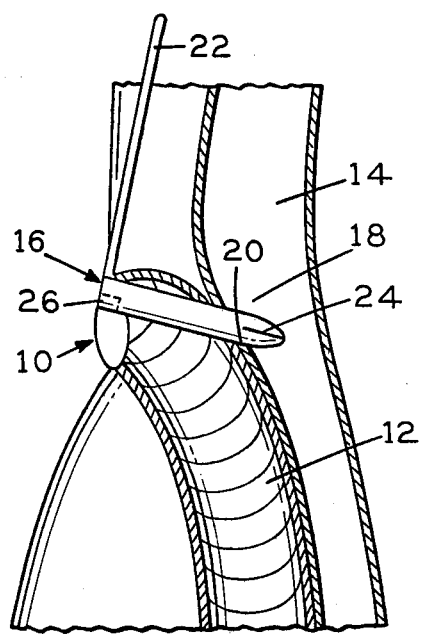
FIG. 1 is a cross section of the trachea and esophagus in a patient who has undergone a laryngectomy showing the apparatus of the invention in place in a fistula.

This danger is alleviated by bringing the trachea to a surgically produced opening or stoma 10 in the neck as shown in FIG. 1. This opening becomes the breathing opening of the windpipe or trachea 12. The stoma 10 is located at the front of the neck just above the breastbone of the patient.

Such an anatomical configuration allows material to pass down through the esophagus 14 without any danger of entering the lungs. The chief difficulty with this configuration, however, is that there is no way for air from the lungs to enter the esophagus and the remainder of the speech tract; that is the pharynx, mouth, and sinus cavities, which all contribute to the quality of speech.

The apparatus 16 of the present invention as illustrated in FIG. 1 comprises an air tube 18 which is inserted in a surgically-formed fistula 20 from the trachea 12 to the esophagus 14. The apparatus includes flange 22, which is formed in a plane extending perpendicularly from the air tube. Flange 22 has a surface which lies on an external portion of the neck. One-way slit valve 24 disposed at the normally closed esophageal end of air tube 18 opens only when the tracheostome or stoma 10 is sealed by the user (typically by placing his thumb over the opening) and the user exhales thus forcing air from the trachea 12 through opening 26 in the underside of air tube 18 and then through slit valve 24.

Apparatus 16 should be formed of a resilient, high-performance elastomeric material such as silicone rubber. It should be of a material which does not irritate the tissues of the body and is itself not degraded by being exposed to body tissues and fluids. The tear strength should be relatively high, for example, die B 150 ppi (pounds per inch). A preferred material is Dow Corning SILASTIC ®Q7-4840 A/B medical grade silicone rubber. This material has a durometer of Shore A 40, a tensile strength of approximately 950 psi, and elongation of approximately 425 percent. It is understood that other higher strength elastomers, particularly silicone rubbers, such as SILASTIC medical grade MDX-4-4515, may also be used, but the life of the device will be significantly reduced, as its tear strength is not as high as that of a high-performance silicone rubber.

Figure 2:
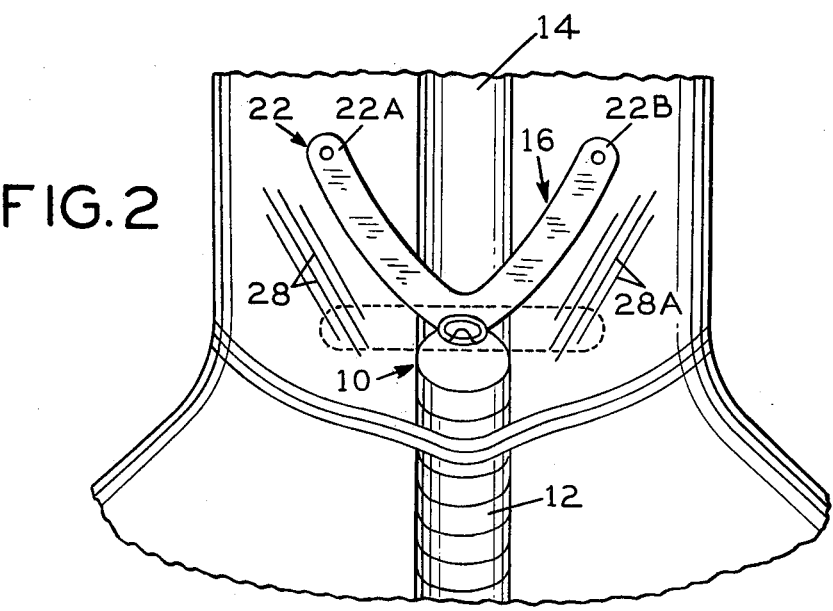
FIG. 2 is a front elevational view of the apparatus as shown in FIG. 1 secured to the neck of the user.

A front view of the neck of the user showing the apparatus 16 of the invention in place is shown in FIG.2. For clarity internal structures such as the trachea 12, the esophagus 14, and the sternal cleidomastoid muscles 28 and 28A are shown in full lines even though, as will be understood by one skilled in the art, these are internal anatomical structures. Flange 22 is comprised of wings 22A and 22B which form a V-shaped structure extending up along the neck. While a more direct approach would seem to be having the wings of the flange extend horizontally as shown in dotted lines in FIG. 2, there is the distinct disadvantage that the flange must cross the medial clavicular heads of the sternal cleidomastoid muscles 28 and 28A. These muscles tense whenever the head is rotated downward bulging out from the neck and tending to eject the attached air tube from the fistula. The configuration of wings 22A and 22B shown in FIG. 2 avoids this problem.

Another problem which is avoided by the wing configuration shown in FIG. 2 is extensive blockage of the stoma 10. The flange occupies a portion of the plane generally perpendicular to air tube 18 but does not cover or obstruct any portion of the stoma 10. This is expecially important in individuals where the stoma is of a small diameter and the introduction of the air tube will in and of itself obstruct a significant percentage of the area of the stoma. The configuration illustrated in FIG. 2 obstructs only a small percentage of the stoma, thus leaving most of the area unobstructed and available for the passage of air.

Figure 3:
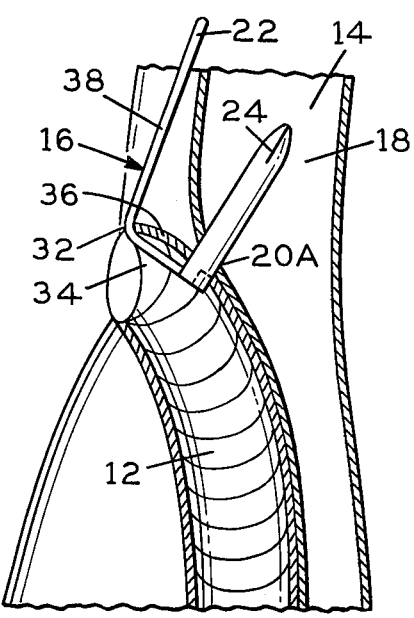
FIG. 3 is a cross section of the trachea and the esophagus showing the apparatus in place in a fistula located at a position in the trachea higher than that shown in FIG. 1.

FIG. 3 illustrates an alternate position for a fistula 20A located further up along the trachea than fistula 20 of FIG. 1. In this embodiment, air tube 18 of apparatus 16 is angled upwardly in the esophagus 14. Flange 22, bent at point 32 has a portion 34 within the trachea and extending generally parallel to tracheal wall 36 and a portion 38 which may be adhesively attached to the neck of the user. Such adhesive fastening may be accomplished by applying Tincture of Benzoin externally to the surface of wings 22A and 22B which contact the neck allowing the material to dry and become tacky, pressing the flanges against the external surface of the neck and then, if desired, covering the flanges and the adjacent external surfaces of the neck with an appropriate tape.

One advantage of the configuration shown in FIG. 3, other than it being a preferred surgical site in certain patients, is that a single size or length of air tube 18 can be used to fit all patients. Air tube 18 will not be long enough when angled upwardly as shown in FIG. 3 to contact and irritate the rear of the esophagus 14. In addition, the end having slit valve 24 will not be embedded in the esophageal wall and will be free to operate, opening during expiration, and closing to keep food or liquids from entering the trachea.

To assure a proper fit and reproducability of the positioning of apparatus 16, it is preferred that flange 22 be malleable. In other words it must retain its shape when it is removed from the patient for cleaning.

FIG. 4 which shows apparatus 16 in partial cross section, illustrates one approach to making flange 22 malleable. A malleable planar material 40 is embedded in the flange parallel to the surface which lies on the neck of the user. In FIG. 4 this material is a thermoformed plastic. This plastic sheet 40 is placed in a mold before the elastomer which forms apparatus 16 is injected into that mold. When the surgeon has determined the proper dimension the bend may be formed by heating the flange in some manner, such as by placing it in a hot bed of sand and then bending the flange at point 32 in a suitable fixture. The apparatus is then permitted to cool, and the flange will remain in its bent configuration until reheated.

A suitable fillet 42 is formed between the flange and the air tube 18 to enhance strength.

The mold which is used to form apparatus 16 may be configured so that a thin, flexible circular flange 44 is provided as an integral part of apparatus 16. Flange 44 may be forced through the fistula so as to be disposed within the esophagus to aid in retaining tube 18 within the fistula if preferred. If the surgeon does not prefer to make use of circular flange 44, it may simply be removed by being cut off with a scissor or sharp edge.

Air tube 18 may be formed with a slight curvature as illustrated in FIG. 4. For some locations of the trachealesophageal fistula this curvature will avoid the problem of the esophageal end of air tube 18 contacting the rear of the esophageal.

Slit or flapper valve 24 may be formed by cutting the otherwise closed end of air tube 18 in the direction of its longitudal axis.

Some surface adhesion generally exists between the contacting surfaces of valve 24. This tend to increase the pressure needed to open valve 24. This adhesion can be reduced by a suitable adhesion-reducing coating 46. When the material of which apparatus 16 is comprised is a silicone rubber, then a fluorosilicone lubricating oil such as DOW CORNING ®FS-1265 fluid may be used. This fluid is comprised of trifluoropropyl-polysiloxane. To apply such a coating, the contacting surfaces of the valves are soaked in an ultrasonic bath at room temperature for approximately 30 minutes. The solvent used in the bath while capable of diffusing into the silicone rubber causing a slight swelling should not significantly degrade the properties of the silicone rubber. Isopropyl alcohol satisfies these requirements while also serving as a solvent for the FS-1265. The contacting surfaces of the valve are then soaked for three to six minutes in a 5 percent solution of 300 centistoke DOW CORNING ®FS-1265 fluid disolved in isopropyl alcohol. This permits the FS-1265 to penetrate into the slightly swollen silicone rubber providing a diffused coating 46 which reduces the adhesion between the contacting surfaces of the valve.

A further reduction in the adhesion may be accomplished by abrading or buffing the contacting surfaces of valve 24 on a vibrating grinding stone. This reduces the effective area of contact thus lowering the adhesive force. This step may be executed before or after the application of the adhesion-reducing compound or coating. The roughening 48 of the contacting surfaces is illustrated in FIG. 5 which shows the slit valve open. The angle of opening has been greatly exaggerated in FIG. 5 for purposes of illustration.

FIG. 6 illustrates another embodiment of the invention. Apparatus 50 is of basically similar structure to apparatus 16. Flange 52, however, has a slightly different configuration with a neck 54 and wings 56 and 58. Malleable characteristics are imparted to flange 52 by including a metal screen or mesh 60 comprised of an implant grade 316 annealed stainless steel per ASTM specification A240. The mesh size and thickness of the wires forming the mesh are not particularly critical, as long as the mesh is completely embedded within the silicone rubber body of apparatus 50 and a malleable flange which is relatively easy to form but maintains its shape after being so formed is produced. Two holes 61 and 63 are provided for positioning mesh 60 in the mold used to produce apparatus 50 as is well known in the art. Circular flange 62 is provided (as is flange 44 in FIGS. 4 and 5) but is optional. Slit 64 and air opening 66 are identical in construction to slit 24 and air opening 26 of apparatus 16.

The elliptical cross section of the air tube combined with the valve slit 64 being formed in the plane in which the longer axis of the ellipse lies assures maximal air flow and minimal opening pressure. This configuration reduces the bending moment of the portions of tube 68 on either side of slit 64 thus contributing to a reduction in the pressure required to acheive the air flow necessary for good quality speech. The ratio of the length of the major axis of the ellipse to that of the minor axis should preferably be between one and one half to three to one. It is shown as being approximately two to one. While a ratio of two to one seems optimum, it is recognized that a higher ratio, for example three to one, would result in a device having a lower opening pressure. The tortional rigidity of the air tube would be reduced, however, and the lateral stability possibly degraded to the point where valve 24 could close with improper alignment between the contacting surfaces. This would not produce a proper seal and could result in material in the esophageal centering the trachea. The selected ratio is maintained along the tapered portion 69 of air tube 68.

Referring to FIG. 7 dimension L represents the length or the air tube. In the preferred embodiment it is approximately 1.20 inches (3.05 cm) long. The wall thickness of the air tube is approximately 0.060 inches (0.152 cm) but tapers slightly as the slit valve is approached as may be more readily appreciated by reference to FIGS. 4 and 5. This taper also serves to facilitate operation of valve 24. The extent of the taper is limited by the practical difficulties associated with molding of the apparatus. As may be seen with reference to FIG. 8 air opening 66 has a length or dimension X of approximately 0.250 inches (0.635 cm) in the direction of the longitudinal axis of tube 68. The slit valve is defined by a cut approximately 0.313 inches (0.794 cm) long.

FIG. 9 is an enlarged view of an additional embodiment of the invention. The construction of apparatus 70 is basically similar to that of apparatus 16 and apparatus 50. In apparatus 70 flange 72 having wings 74 and 76 is rendered malleable by virtue of a thin sheet of metal 78. This metal sheet may be comprised of aluminum, titanium or preferably implant grade 316 annealed stainless steel as is screen 60 of apparatus 50. This sheet may be anywhere from 0.005 inches to 0.015 inches thick; the latter thickness however being preferred to form a fairly rigid but malleable flange.

Before being inserted in the mold used to form apparatus 70, sheet 78 is placed in a sand tumbler for a period of time sufficient to remove all sharp edges. Two holes 80 and 82 are then punched in sheet 78 to mate with protrusions within the mold which serve to properly position sheet 78. Before molding, however, sheet 78 is surrounded by a DACRON mesh 84 which along with the blunting of sharp edges on sheet 78 serves to prevent sheet 78 from migrating and cutting through the elastomer cast around sheet 78.

FIG. 10 shows a cross section of wings 74 of flange 72. Metal sheet 78 is shown as being surrounded by dacron mesh 84 which may be in the form of a "sack" into which sheet 78 fits. The elastomeric material from which apparatus 70 is formed is then cast around the composite structure of sheet 78 and dacron mesh 74 as shown.

The apparatus of this invention will generally be of a long, trouble free life if properly maintained. It must be removed as required for cleaning by washing in warm running water to remove encrustation. Solvents or petroleum based products which may damage the silicone rubber should never be used. The apparatus should be put back in place after cleaning because extended removal will permit the fistula to close, necessitating surgical reopening.

Various other applications and modifications of the invention in addition to those described herein will become apparent to one skilled in the art from the above drawings and description which have been offered by way of illustration only and not in limitation of the invention, the scope of which is defined in the appended claims.

We claim:

1. A prosthesis to assist esophageal speech in a laryngectomee having a tracheostome and a tracheal-esophageal fistula comprising:

(a) an elastomeric bio-compatible silicone rubber air tube with an open tracheal end and a normally closed esophageal end having an elliptical cross section with major and minor axes and a one-way slit valve located along the plane of said major axis at the esophageal end of said tube, the elliptical cross section of that portion of the tube containing the slit valve being progressively tapered downwardly in size between the section containing the end of the slit valve nearest the tracheal end and the section containing the end of the slit valve at the esophageal end of said tube, and the ratio of the lengths of the major and minor axes of said elliptical cross section being between 1.5 to 1 and 3 to 1;

(b) a flange formed in a plane extending generally perpendicularly from said air tube adapted to occupy a sufficiently small portion of said plane so as to have a surface which lies on an external portion of the neck without covering the portion of the neck having the tracheostome.

2. The apparatus of claim 1 in which the contacting surfaces of said slit valve are coated and impregnated with an adhesion-reducing compound.

3. The apparatus of claim 2 in which the adhesion-reducing compound is trifluoropropylpolysiloxane.

4. The apparatus in accordance with claim 1 in which the wall thickness of the elastomer tube in that portion of the tube containing the slit valve is progressively tapered downwardly in thickness between the section containing the end of the slit valve nearest the tracheal end and the section containing the end of the slit valve at the esophageal end of said tube.

5. The apparatus of claim 1 in which the flange comprises a substantially V-shaped member configured to avoid covering the area of the neck of the user associated with sternal cleidomastoid muscles.

6. The apparatus of any one of claims 1–5 further including a flexible retainer flange surrounding and extending generally perpendicularly from the air tube and capable of being inserted through the fistula into the esophagus to aid in retaining the tube within the fistula.

* * * * *

UNITED STATES PATENT AND TRADEMARK OFFICE
CERTIFICATE OF CORRECTION

PATENT NO. : 4,439,872
DATED : April 3, 1984
INVENTOR(S) : Julian L. Henley-Cohn and Eugene R. Jakubczak Page 1 of 2

It is certified that error appears in the above—identified patent and that said Letters Patent is hereby corrected as shown below:

Column 1, line 44, "U.S. Patents 4,060,402 and" should read --U.S. Patents 4,044,402 and--;

Column 1, line 44, "Nigel" should read --Edwards--;

Column 2, line 6, "ocassionally" should read --occasionally--;

Column 3, line 45, "such as silicone" should read --such as a silicone--;

Column 5, line 11, "esophageal" should read --esophagus--;

Column 5, line 33, "disolved" should read --dissolved--;

Column 6, line 5, "acheive" should read --achieve--;

Column 6, line 13, "tortional" should read --torsional--;

UNITED STATES PATENT AND TRADEMARK OFFICE
CERTIFICATE OF CORRECTION

PATENT NO. : 4,439,872

DATED : April 3, 1984

INVENTOR(S) : Julian L. Henley-Cohn and Eugene R. Jakubczak

It is certified that error appears in the above—identified patent and that said Letters Patent is hereby corrected as shown below:

Column 6, line 18, "esophageal" should read --esophagus--;

Column 6, line 18, "centering" should read --entering--;

Column 6, line 22, "or" should read --of--;

Column 6, line 62, "dacron mesh 74" should read --dacron mesh 84--.

Signed and Sealed this

Twenty-first Day of August 1984

[SEAL]

Attest:

Attesting Officer

GERALD J. MOSSINGHOFF

Commissioner of Patents and Trademarks